United States Patent [19]

Delmenico

[11] Patent Number: 5,658,239
[45] Date of Patent: Aug. 19, 1997

[54] METHOD AND APPARATUS TO ESTABLISH TARGET COORDINATES FOR LITHOTRIPSY

[76] Inventor: Peter R. Delmenico, 2520 Marcy Ave., Evanston, Ill. 60201-1112

[21] Appl. No.: 658,893

[22] Filed: May 31, 1996

Related U.S. Application Data

[63] Continuation of Ser. No. 538,442, Oct. 3, 1995, abandoned, which is a continuation of Ser. No. 378,681, Jan. 26, 1995, abandoned, which is a continuation of Ser. No. 881,515, May 12, 1992, abandoned.

[51] Int. Cl.$^6$ .................................................. A61B 17/22
[52] U.S. Cl. ............................................ 601/4; 128/660.03
[58] Field of Search ................... 601/2, 4; 128/660.03; 73/620, 625, 627, 628, 634, DIG. 1

[56] References Cited

U.S. PATENT DOCUMENTS

| | | | |
|---|---|---|---|
| 3,676,584 | 7/1972 | Plakas et al. | 601/2 |
| 4,094,306 | 6/1978 | Kossoff | 601/2 |
| 4,764,944 | 8/1988 | Finlayson | 378/20 |
| 4,805,622 | 2/1989 | Riedlinger et al. | 128/660.06 |
| 4,834,074 | 5/1989 | Reichenberger | 601/4 |
| 4,957,099 | 9/1990 | Hassler et al. | 128/660.03 |
| 4,991,604 | 2/1991 | Wurster et al. | 128/660.03 |
| 5,009,232 | 4/1991 | Hassler et al. | 601/4 |
| 5,122,993 | 6/1992 | Hikita et al. | 128/662.03 |
| 5,431,621 | 7/1995 | Dory | 601/4 |

FOREIGN PATENT DOCUMENTS

| | | | |
|---|---|---|---|
| 8703797 | 7/1987 | WIPO | 601/4 |
| 0002724 | 4/1989 | WIPO | 601/4 |

*Primary Examiner*—Brian L. Casler
*Attorney, Agent, or Firm*—McDonnell Boehnen Hulbert & Berghoff

[57] ABSTRACT

The invention discloses a method and apparatus for effectively localizing a stone and targeting a shock wave in connection with extracorporeal shock wave lithotripsy ("ESWL"). The technique disclosed by this invention can be adapted for use in connection with any conventional lithotripter. In this invention, an array of at least 3 and preferably 4 or more pressure transducers are used to sense the reflection from the target in response to an initial shock wave or ultrasonic wave. The sensor readings are then temporally shifted relative to one another in such a way as to maximize correlation between the signals from each sensor. The required time shifts for maximum correlation are used to calculate the differences in arrival times of reflected waves at the sensors. By knowing the original location of the sensors and establishing the time differences at which the reflected wave reaches the different sensors, a technique is disclosed to determine the vector coordinates extending between the target location and the focal point of the lithotripter.

19 Claims, 3 Drawing Sheets

METHOD AND APPARATUS TO ESTABLISH TARGET COORDINATES FOR LITHOTRIPSY

This is a continuation of application Ser. No. 08/538,442, filed Oct. 3, 1995 now abandoned, which is a continuation of Ser. No. 08/378,681, filed Jan. 26, 1995, abandoned, which is a continuation of Ser. No. 07/881,515 filed May 12, 1992, abandoned.

FIELD OF THE INVENTION

This invention relates to improvements in the field of lithotripsy. More particularly, the invention discloses a technique by which the location of the target stone can be established more efficiently and effectively for extracorporeal shock wave lithotripsy ("ESWL"), such that the stone can be more effectively eliminated.

BACKGROUND

A. General Principles

ESWL is a non-invasive technique for destroying biliary and renal concretions, i.e., stones, using acoustic shock waves. The shock waves are generated externally to the patient and focused on the site of the stone. During ESWL treatment the stones are fragmented into pieces small enough to either pass out of the body through normal excretory channels (ureter or bile ducts) or respond favorably to chemical dissolution treatment.

The use of sound waves for ultrasound and electrohydraulic lithotripsy by direct contact with the target was well established prior to ESWL. However, the use of shock waves in ESWL is different. Ultrasound consists of sinusoidal waves of defined wave length, with alternating positive and negative deflections. Shock waves consist of a single positive pressure front of multiple frequencies with a steep onset and a gradual decline.

Shock waves undergo less attenuation than ultrasound waves when propagated through water or body tissue. As a result, shock waves can be transmitted through water and into the body with little loss of energy or damage to tissue.

The use of shock waves in the medical field for the destruction of urinary stones is based on the following properties:

1. Shock waves give rise to mechanical stress in brittle materials, such as human kidney stones.
2. Shock waves lead to disintegration of such brittle material.
3. Shock waves generated by the underwater discharge of a capacitor can be reliably reproduced.
4. Shock wave energy can be propagated through water bath and body tissue to the stone with minimal energy loss or damage to tissue.
5. Shock waves can be precisely focused by integrating the energy source with a suitable reflecting system.

Based on these principles, repeated shock wave stress will eventually exceed the comprehensive strength of the stone and lead to its disintegration.

Once the focused shock wave reaches the stone, the pressure front is partially reflected at the front surface of the stone, thus producing compressive and tensile components, which leads to buildup of a high-pressure gradient and causes disintegration of the stone's front surface. A portion of the wave continues through the stone and is reflected at the rear surface, where the same effect takes place. The disintegration of the outer layers exposes new surfaces that in turn are broken into fragments. This process eventually results in the complete disintegration of the entire stone.

In addition to the compressive forces and the negative tensile forces, cavitation microjets contribute to calculus fragmentation. Acoustic cavitation occurs when the tensile forces exceed ambient pressure, pulling apart the liquid and creating a bubble that collapses with the return of positive pressure.

B. Lithotripter Designs

Shock waves are created by converting energy into an acoustic form. The currently available extracorporeal shock wave lithotripters use energy sources that are electrohydraulic, piezoelectric, electromagnetic, or explosive in nature. Shock waves are focused on the stone by ellipsoidal reflectors, shaped array, or lens. Localization of the stone is by x-ray and/or ultrasound studies.

With the electrohydraulic method, electricity is discharged into water across a gap between two electrodes. The temperature of the water rises rapidly to form steam and then a plasma. A compressive pressure pulse results from expansion of the heated gases, followed by a negative pressure pulse as the gas bubble collapses. In the piezoelectric machines, an electrical field is applied across a piezoelectric crystal, changing the external dimensions of the crystal. Pressure waves are produced by the movement of the crystal. Multiple crystals are used in the machines for reliability and ease of construction. In the electromagnetic generators, a magnetic field is generated by current flow through a wire or coil. Magnetic materials are attracted or repelled by this field, turning electrical energy into mechanical and acoustic energy. The pressure wave is created by movement of a flexible membrane from passage of current through a fixed coil.

Focusing is accomplished geometrically by an ellipsoidal reflector in many machines. The shock waves created at the first focus of the ellipsoid by the generation system are reflected by the ellipsoidal reflector to arrive at the second focus simultaneously creating a shock wave at the final focal point. In the Siemens electromagnetic lithotripter, the sound waves are focused by biconcave acoustic lens. In the piezoelectric lithotripters, the crystals are shaped as part of a sphere to focus the energy.

In order for the shock wave to effectively destroy the stone, the site of the stone must be coincident or nearly coincident with the final focal point of the generated shock wave. This is accomplished by first, localizing the site of the stone in relation to the geometric focal point of the shock wave and, then, targeting (or adjusting) the location of the stone so as to be coincident with the focal point of the shock wave.

The targeting of the stone in relation to the focal point of the shock wave is conventionally accomplished by physically adjusting the position of either the patient or the shock wave generating system, until the location of the stone is determined to be coincident with the geometric focal point of the shock wave generating system. Although somewhat cumbersome, this method of adjustment has proven useful in conventional lithotripsy.

Difficulty has existed in locating the stone and accurately identify that location in relation to both the geometric focal point and, more importantly, the acoustic focal point of the machine. Stones are typically located using ultrasonography or x-ray flourography, with the image of the stone being displayed on a videoscope or x-ray image. A computer generated image, denoting the geometric focal point of the shock wave, may be superimposed on the ultrasound video display or x-ray image as a targeting aid. However, this technique of localizing and targeting has proven inadequate in several respects.

Ultrasound has the advantage of being able to be used continuously, but the disadvantage that stones cannot be visualized in certain locations. Moreover, ultrasound requires a considerable learning curve and sometimes it is difficult to determine the degree or fragmentation, in part due to the formation of an echogenic fragment line. Stone localization by ultrasound may be difficult in the kidney in the presence of a percutaneous nephrostomy tube, multiple calculi in the renal pelvis, or partial staghorn calculi. X-ray fluoroscopy is less commonly used and present added health concerns in that some people want strongly to avoid any exposure to x-rays. In addition, fluoroscopy is unable to visualize radiolucent stones such as those common in the gallbladder.

More importantly, the conventional techniques for localizing the stone frequently do not allow effective targeting. In order for the lithotripsy to effectively destroy the stone, the target center or the stone should be positioned as closely as possible to the focal point of the lithotripter. To the end, it is considered advantageous to be able to keep the stone in a region where the peak pressure at the stone site during lithotripsy is at least 50% of the pressure at the focus. For currently available lithotripters, the area in the focal plane described by this 50% isobar can be as small as 3 $mm^2$, as reported by Coleman and Saunders (Ultrasound in Medicine and Biology, 15(3):213–227. (1989)). Conventional techniques of ultrasonography and flourography are problematic when targeting with such a small focal area for a variety of reasons, e.g., imprecision in manually adjusting the physical position of the patient and/or the shock wave focal point, displacement of the acoustic focal point of the generated shock waves from the geometric location due to diffraction effects, and stone visualization errors introduced due to diffraction effects on ultrasound imaging systems. As a result, extracorporeal lithotripsy procedures currently involve the application of between 1500 and 4000 shock waves to the stone site in order to reduce stone fragments to a size that can safely pass through the patient's system, or to be treated successfully using dissolution agents. Such a large number of shock waves prolong the treatment, may require multiple treatments, increase treatment cost, can produce tissue damage, and may require the administration of anesthesia to the patient.

In seeking to reduce the number of shocks applied, conventional targeting techniques have evolved along two diverging paths. One philosophy of improving lithotripters has been to apply more powerful shook waves and increase the volume of the acoustic focal point of the shock waves. This approach has the disadvantage of applying more shock wave energy to the tissue near the stone, with the attendant risk of tissue damage. The other philosophy of lithotripter development is to decrease the shock wave amplitude and decrease the volume of the focal point, the argument being that this method reduces the risk of tissue damage while maintaining the ability to destroy stones. A further advantage of this philosophy is that it makes possible anesthesia-free lithotripsy. However, a reduced focal point volume exacerbates existing targeting problems.

Other improvements in localizing and targeting stones have been recently reported. See Kuwahara et al, "Initial Experience Using a New Type Extracorporeal Lithotripter With An Anti-Misshot Control Device," *J. of Lithotripsy and Stone Disease*, Vol. 3, No. 2, pp. 141–146 (1991). This device is based noon the use of piezoelectric transducers to generate the shock wave, but the piezoelectric transducers are also used in a rudimentary way to assist in localizing the stone. Initial localizing of the stone is performed using an ultrasound sonoprobe installed in the shock wave generator. Ultrasound pulses are directed from the shock wave generator toward the geometric focal point of the shock wave. The sound levels, if any, reflected from the focal point region are detected by the piezoelectric transducers (now acting as a microphone). The signal is judged as a hit or miss based upon the amplitude of the reflected wave, i.e., a high level indicates a hit and a low level indicates a miss. A predetermined threshold is established in a comparator to judge whether the signal is a hit or a miss.

Simply stated, the Kuwahara et al. technique merely provides "yes/no", trial-and-error, information on whether the stone has been accurately sited and targeted. Kuwahara et al. failed to recognize or disclose any guidance adjustment mechanism for determining the direction and amount of movement which is needed to accurately locate and target the stone. Moreover, the technique of Kuwahara et al. is limited to lithotripters which are based upon piezoelectric shock wave generators. Kuwahara et al. does not disclose a guidance adjustment mechanism which is useful in other types of lithotripters.

SUMMARY OF THE INVENTION

Accordingly, it is an object of this invention to provide a technique by which individual shock waves from the shock wave generator can be used to provide accurate information on the coordinate location of a target stone.

It is also an object of this invention to provide a method and apparatus by which individual shock waves from the shock wave generator will provide accurate information on the relative direction and amount of movement needed to accurately target a stone.

A further object of this invention is to provide a method and apparatus by which coordinate data is generated in order to specifically locate the target stone by an in vivo relation to the acoustic focal point of the shock wave.

Another object of this invention is to provide a digital calculation technique by which to control and coordinate the location, targeting, and transmission of shock wave in lithotripsy.

A still further object of this invention is to provide a method and apparatus for precisely targeting the shock waves used in lithotripsy so as to reduce the intensity of the shock waves and/or the number of shock waves needed to effectively conduct lithotripsy.

The invention is generally comprised of two components. The first includes apparatus to detect reflected pressure waves at a plurality of distinct locations and to record and store this information in a form which is suitable for machine analysis. Preferably, this first component will convert the reflected and detected pressure wave into a digital format representation. The second component includes apparatus, preferably but not necessarily computer based, to analyze the recorded and stored information on the reflected shock wave and determine the relative coordinate relationship between the target stone and the focal point of the shock wave.

With further respect to the first component, the detection/recording system preferably includes an array of at least three (3), and preferably four (4) sensors that are mounted around the surface of a shock wave focusing system. The sensors are preferably piezoelectric transducers, but could be any conventional pressure transducer used in measuring shock waves. The sensor locations may be arbitrary, with the constraint that the sensors should preferably be positioned so that they do not share an (x), (y) or (z) relative coordinate position. The accuracy of the system will be substantially improved if this guideline is followed. Four sensors represent the preferred number requirement for location of the stone in three dimensions, however the use of more than four sensors will improve the ability of the system to account for the nonlinear effects of human tissue on shock wave transmission.

Each sensor is preferably connected to a voltage amplifying unit, and the amplified signal is then input to an apparatus that will record and store the signal, such as a digital storage oscilloscope. A digital storage oscilloscope represents only one of a number of methods for the analog to digital conversion and the recording and storage of signals from pressure sensing devices, and the person of ordinary skill will recognize that other such devices will work. For example, an analog integrated circuit could be used.

Triggering of the oscilloscope can be set to occur when some threshold pressure level is reached at one or more of the pressure sensors. Alternatively, the electrical noise produced by the lithotripter during shock wave formation can be used to trigger the oscilloscope. In either case, the oscilloscope is triggered to record the reflected wave once for each initiated shock wave. Once triggered, the oscilloscope acquires and records the signal from each of the sensors over a duration sufficient to ensure that signal representations of the pressure waves reflected from the stone site are adequately captured. For each lithotripter design, the appropriate sample period can be readily determined by experience based on the distance from the sensors to the geometric focus of the lithotripter and the average speed of sound in water and human tissue.

With further respect to the second component of the invention, after each reflected shock wave has been recorded and stored, the stored signals are transferred to a computer. Once the information is accessed by the computer, it is modified according to the following procedure.

1. Each signal is windowed, i.e., chopped, around the arrival time of any reflected pressure waves. The duration of this window is such that the windowed signal comprises the prominent features of the reflected shock wave.
2. The average amplitude of the data points comprising each signal is subtracted from each data point in that signal. In so doing, each signal is shifted such that the average value of the data points in that signal is zero. This operation is equivalent to removing any DC-shift in the signal.
3. The amplitudes of the data points comprising each signal are divided by the signal's maximum positive amplitude within the chosen window. (The maximum positive value of the output from all of the sensors will be identical after this operation.) This normalization scheme facilitates the subsequent analyses.
4. The windowed signal from each sensor is time-shifted with respect to the signals from each of the other sensors, in turn, in such a way that the correlation between the signals is maximized for each combination of sensors. The time shift for maximum correlation is equal to the difference in the time of arrival of the reflected pressure waves at the two sensors. These differences in arrival times (delays in arrival at one sensor with respect to the other) are then stored in the computer's memory for each sensor pairing. Thus, for a system of four pressure sensors, six delay times are calculated.
5. The delay times for each sensor pairing are used to determine the coordinate components of a vector from the geometric focus of the lithotripter to the stone location.

In preferred embodiment of the invention, the computer can also transmit signals to a position adjusting mechanism. This mechanism may adjust the physical position and/or orientation of the patient and/or the shock wave generator so as to superimpose the target stone and the shock wave focal point. The mechanism for responding to the computer and making such adjustment may be of the type readily known to those of ordinary skill in the art once the coordinate information has been determined.

DETAILED DESCRIPTION OF THE INVENTION

This invention suggests, for the first time, that information from a reflected ESWL shock wave can provide the coordinate information to accurately locate the target stone and to adjust the focal point of the shock wave so as to be coincident with the target location.

Because of the greater targeting accuracy that can be accomplished using this invention, target stones can be destroyed using fewer shock waves of lower amplitude. This greatly minimizes the risk of incidental tissue damage to the region surrounding the target.

Due to sound speed variations in human tissue, it is likely that the geometric focal point of the lithotripter will not be coincident with the acoustic focal point, i.e., the location of maximum pressure of the shock wave. Used in an iterative fashion, this invention can be used to locate the acoustic (i.e., effective) focus of the lithotripter for a given patient's anatomy. Such knowledge of the location of actual maximum pressure for individual patients would be a valuable compliment to knowledge of the location of the geometric (i.e., theoretical) focus of the lithotripter.

It is common practice to aid targeting of a lithotripter by superimposing a computer generated reference symbol on the ultrasound or x-ray display as an indicator of the position of the lithotripter's geometric focus. Such geometric reference display could now be supplemented by display of the computer position of the stone and the acoustic focus of the lithotripter.

This invention is compatible with all of the different types of shock wave generation and focusing system that are commonly employed in lithotripters at this time. For example, the integration of pressure sensing devices in the shock wave generation and focusing system of an electrohydraulic lithotripter was described earlier. For use of the invention with electromagnetic generation systems, recommended placement of the pressure transducers, or sensors, would be a location between the patient and the acoustic lens, rather than between the acoustic lens and the shock wave source. Sensors should be rigidly attached to the focusing system at predetermined positions such that the sensors lie outside of the transmission path of shock waves being focused at the target site, but are in the path of reflected pressure waves. As another example, this invention could be integrated most easily with piezoelectric generation systems, since the same piezoelectric crystals that are used to generate the shock waves can be used to detect reflected pressure waves.

Figure 1:
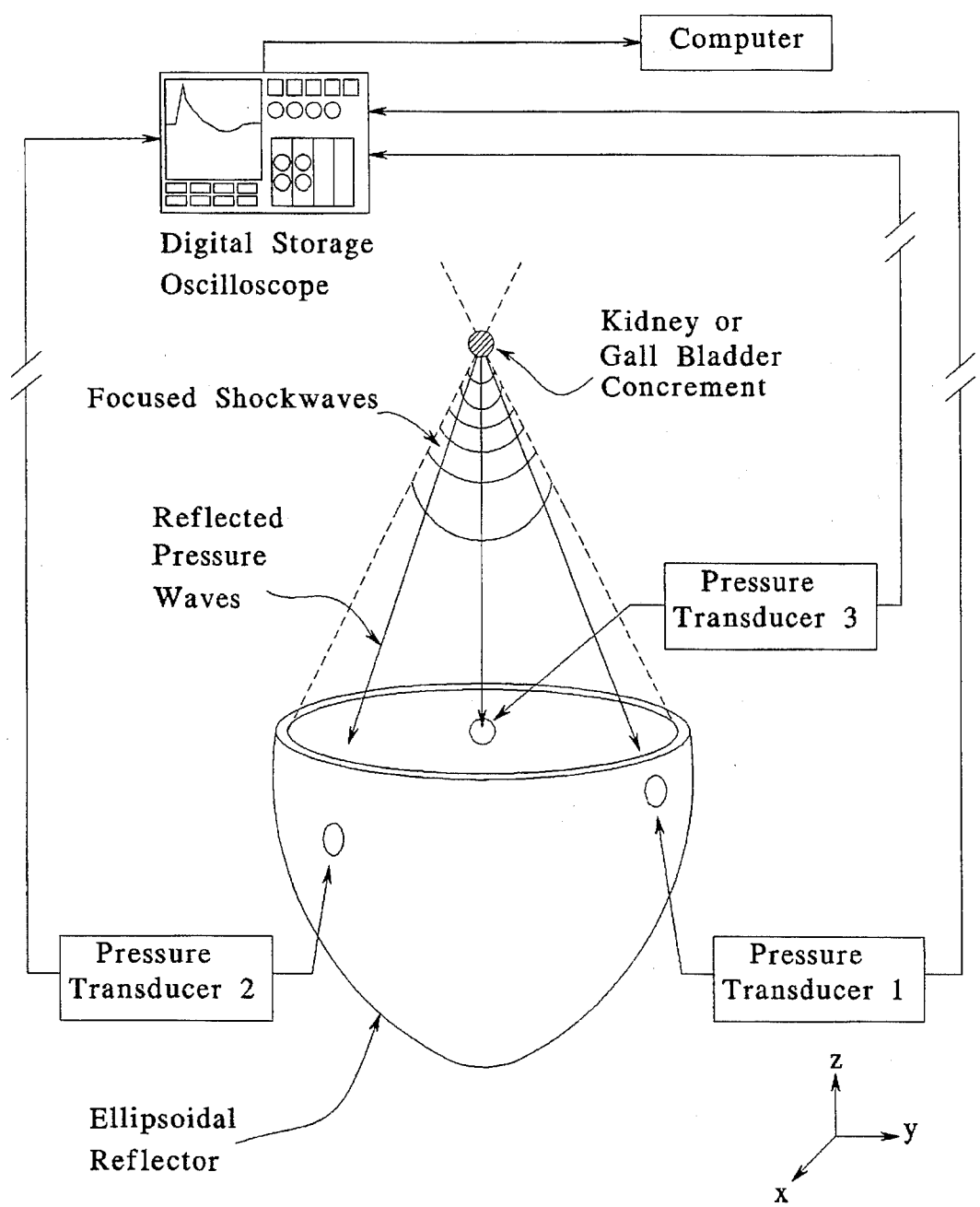
FIG. 1 shows a schematic illustration of an ellipsoidal focusing system using the invention in a 3-transducer configuration.
Figure 2:
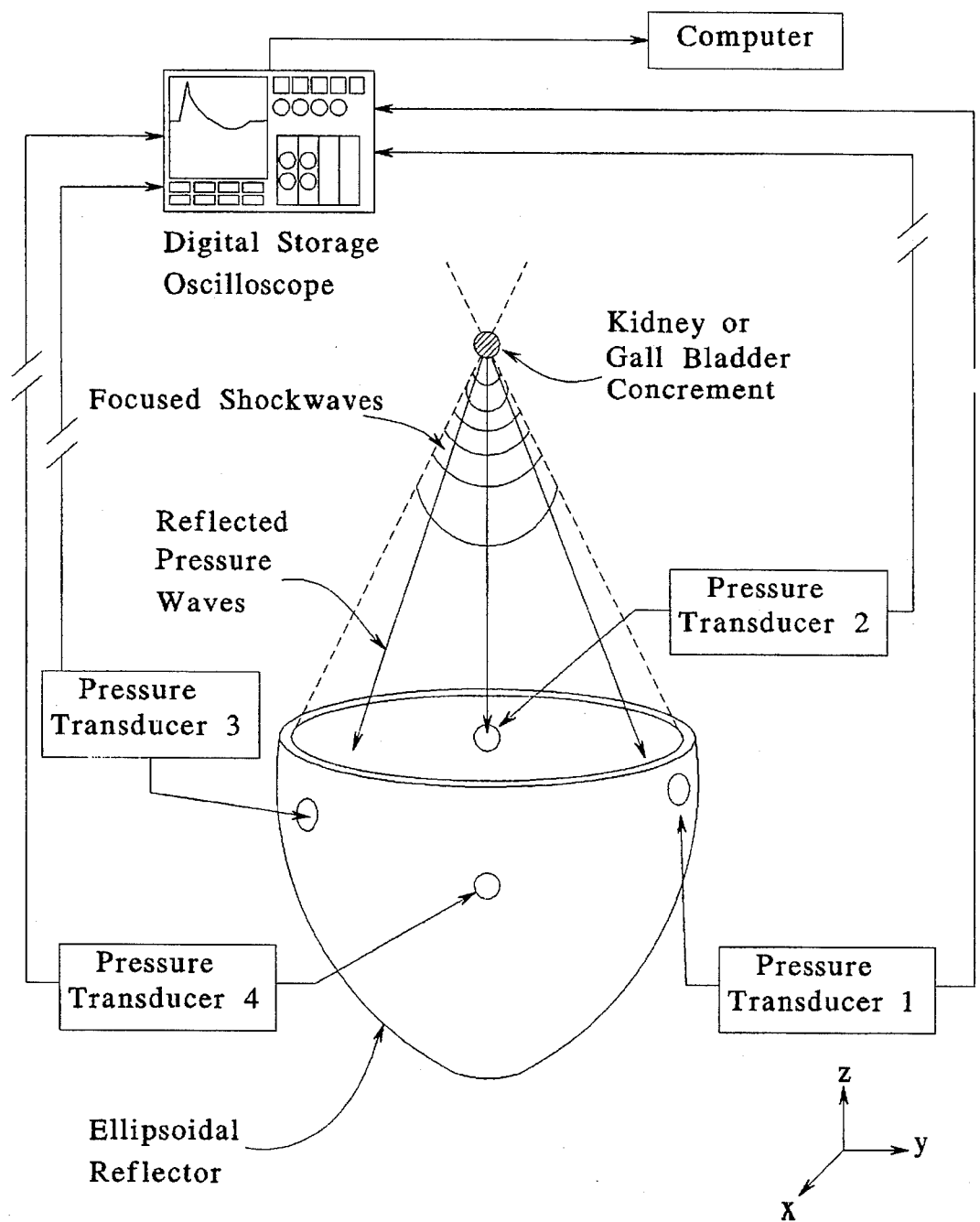
FIG. 2 shows a schematic illustration of an ellipsoidal focusing system using the invention in a 4-transducer configuration.

FIGS. 1 and 2 provide schematic illustrations in connection with a spark gap lithotripter. The shock wave is initiated by the generator and focused by the ellipsoidal reflector toward the general direction of the target. As the shock wave bounces off the target, reflected waves travel toward the sensors. The sensors respond by creating electrical signals which are transmitted to and stored by the digital storage oscilloscope. The digital storage oscilloscope converts the analog signals of the sensors to a digital signal. These digital signals are then transmitted to a computer which processes them in the manner to be described shortly. The result is that the computer derives accurate information for the x, y, z coordinates of the stone in relation to acoustic focal point of the stone. This information can be displayed on the oscilloscope and/or input to adjust the focal point.

A. DERIVATION OF EQUATIONS FOR COMPUTING COORDINATE INFORMATION

Having the general technique to use pressure waves reflected from a target as an indicator of targeting accuracy, we now derive the necessary equations for computing the coordinate information. First consider some desired target location, generally taken as the geometric focus of the applied shock waves, the location of which will be denoted by the cartesian position vector $\vec{x}_o = (x_o, y_o, z_o)$. As noted earlier, due to nonlinear acoustic effects, the location of maximum pressure may not be coincident with the geometric focus of the lithotripter. The transducers for measurement of reflected pressures will be located by the vectors $\vec{x}_n = (x_n, y_n, z_n)$, where n ranges from 1 to the number of transducers. The actual location of the target will be represented in a similar fashion by $\vec{x} = (x, y, z)$.

Two equations are written for each transducer:

$$d_n^o = \sqrt{(\vec{x}_o - \vec{x}_n)^2} \text{, and} \quad (1)$$

$$d_n = \sqrt{(\vec{x} - \vec{x}_n)^2} \quad (2)$$

The first equation represents the distance between the transducer and the geometric focus, which is a known quantity of the focusing geometry. The second equation represents the distance between the transducer and the target location. Expanding the second equation in a Taylor series around $\vec{x} = \vec{x}_o$ and taking only the linear terms, we get, $$d_n(\vec{x}) = d_n|_{\vec{x}_o} + \vec{\nabla} d_n|_{\vec{x}_o} \cdot (\vec{x} - \vec{x}_o) + \ldots, \quad (3)$$

where the first terms is $d_n^o$, or the distance from the nth transducer to the acoustic focus. If we now let $\epsilon$ denote the difference $(\vec{x} \cdot \vec{x}_o)$, equation (3) simplifies to, $$d_n(\vec{x}) = d_n^o + \vec{\nabla} d_n|_{\vec{x}_o} \cdot \vec{\epsilon} + \ldots \quad (4)$$

Evaluating the second term in (4), $$\vec{\nabla} d_n|_{\vec{x}_o} \cdot (\vec{x} - \vec{x}_o) = \vec{\nabla} d_n|_{\vec{x}_o} \cdot \vec{\epsilon} = a_n \epsilon_x + b_n \epsilon_y + c_n \epsilon_z, \quad (5)$$

where we have substituted the scalar components, $\epsilon_x, \epsilon_y,$ and $\epsilon_z$ for target position vector $\epsilon$. The coefficients $a_n, b_n,$ and $c_n$ are given by, $$a_n = \frac{\partial d_n}{\partial x}\bigg|_{\vec{x} = \vec{x}_o} = \frac{1}{2} \frac{2(x_n - x)}{d_n}\bigg|_{\vec{x} = \vec{x}_o} = \frac{(x_n - x_o)}{d_n^o}, \quad (6)$$

$$b_n = \frac{(y_n - y_o)}{d_n^o}, \text{ and} \quad (7)$$

$$c_n = \frac{(z_n - z_o)}{d_n^o} \quad (8)$$

Clearly, the coefficients $a_n, b_n,$ and $c_n$ can be calculated provided the placement of the sensors and the acoustic focus are known. It follows then that the components of the target position vector can be determined using (9), provided that at least three sensors are used.

$$d_n = d_n^o + a_n \epsilon_x + b_n \epsilon_y + c_n \epsilon_z \quad (9)$$

When applied to the problem of lithotripsy, however, equation (9) proves to be difficult to evaluate. Although it is possible to solve the problem if a minimum three sensors are used, it is particularly advantageous to use four sensors, from reasons which will become clear as follows.

To determine $d_n$, the output of the sensors is acquired during the delivery of a single shock wave. The component of the shock wave that is reflected from the target is identified for each sensor, based partially on the pressure wave's characteristic shape, and partially on the expected arrival time. In the linear case, the arrival time is a function solely of the distance from the sensor to the target, so equation (9) can be used to determine the target location. The problem is in finding a feature of the reflected pressure wave that can be used in programming a computer to correctly identify the arrival time. Rather than take this approach, (9) can be rewritten as a difference equation between pairs of sensors, so that, $$d_n - d_m = d_n^o - d_m^o + (a_n - a_m)\epsilon_x + (b_n - b_m)\epsilon_y + (c_n - c_m)\epsilon_z \quad (10)$$

A disadvantage of this formulation of (10) is that a minimum of four sensors are needed to calculate the position of the target. This equation is preferable, however, because determination of the value of $d_n - d_m$ can be done without prior knowledge of the shape of the reflected pressure wave. To illustrate, we can compute the time shift needed to provide the best correlation between the output of sensors (1) and (2), windowed around an expected arrival time. This corresponds to the difference in arrival times between sensors. Given a window of short duration, the arrival of the pressure wave can experimentally be shown to be the dominant feature in the windowed data, allowing an accurate calculation of relative delay times. This information can then be used to determine the target location, provided that at least three linearly independent versions of (10) can be written using pairs of pressure transducers.

In the case where more than three linearly independent equations can be written for the three unknowns, the overdetermined systems can be solved numerically using the pseudo-matrix inverse method, or any other method appropriate for solving overdetermined systems. Consider first a set of difference equations, $$\underline{Ax} = \underline{b} \quad (11)$$

For an overdetermined system, $\underline{A}$ will have m rows and n columns, where m is the number of sensors and n is the number of directions needed to describe the displacement of the target. Measurement errors can be written in equation (11) as an error vector, $\underline{E}$, such that, $$\underline{Ax} - \underline{b} = \underline{E}, \text{ where } \underline{E} = \begin{Bmatrix} e_1 \\ e_2 \\ \cdot \\ \cdot \\ \cdot \\ e_m \end{Bmatrix} \quad (12)$$

Now find $\underline{x}$, such that the equation $e_1^2 + e_2^2 + \ldots + e_m^2$ is minimized. It can be proved that such a solution for $\underline{x}$ is given by, $$\underline{x} = (\underline{A}'\underline{A})^{-1}\underline{A}'\underline{b}. \quad (13)$$

This method can also be used to determine the acoustic focus of the lithotripter. For the purposes of this argument, the phrase "geometric focus" will be used to refer to the far focus of a perfect semi-ellipsoid, while the phrase "acoustic focus" will refer to the point in space at which singly reflected shock waves converge simultaneously. The present discussion considers a focusing system utilizing a geometrically perfect semi-ellipsoid, with a pressure point source located precisely at the near focus. Also, the present discussion uses a ring of pressure transducers located equidistant from the near focus, spaced around the aperture of the ellipsoid. By the definition of an ellipsoid, all ray paths that connect the two foci and include a single reflection from the ellipsoid will have the same length, regardless of the reflection point. This is also assumed to hold true for acoustics in a homogeneous transmission medium. When a homogeneous transmission medium is assumed, the geometric and acoustic foci will be considered to be coincident.

As a next step in the assumptions, replace the homogeneous medium with one that is homogeneous between the near focus and the transducers, and inhomogeneous between the transducers and the far focus. This is a more accurate representation of in vivo conditions. Folberth and Hassler, European Urology, 18:215–221 [1990], have shown through computer simulations that inhomogeneities encountered in vivo caused deflections in the acoustic waves of both ultrasound system and lithotripters. Such deflections are also predicted by the theories of nonlinear acoustics. Therefore, it is no longer accurate to assume that the geometric and acoustic foci will be coincident.

Using the method developed earlier, the pseudo matrix inverse method calculates a least-squares solution to the overdetermined system of delay equations, providing information on the shift necessary to bring the stone to the geometric focus. As recognized by this invention, there are two target locations at which the computed values of needed shift will be minimized, i.e., approximately zero. These are the geometric focus and the acoustic focus. The first is a consequence of the method used to formulate the equations, while the second is an outcome of the nonlinear effects of the inhomogeneous medium.

Refer now to the previous definition of the acoustic focus as the point at which singly reflected shock waves converge simultaneously. This definition requires equal transmission times along all rays connecting a transducer and the acoustic focus, regardless of the curvature of those rays. If the target were now considered to be a pressure point source and the direction of transmission along the original ray paths reversed, it would follow that transmission times from the acoustic focus to the transducers must still be equal. Therefore, all transducers will detect the arrival of the reflected shock wave at the same time, and the relative detection delay between any two sensors will be minimized, i.e., approximately zero. Subsequently, with an overdetermined system set equal to zero and nonzero values of a, b, and c, the least-squares solution of the system must then be $e_x \approx e_y \approx e_z \approx 0$. The most important aspect of this result is that the invention will calculate $e_x \approx e_y \approx e_z \approx 0$ for a stone at the acoustic focus, regardless of sound—speed variations is vivo. Therefore, when the invention is used to make iterative adjustments to targeting, the acoustic focus of the lithotripter will be located.

B. Method for Determination of Delay Times

Figure 3:
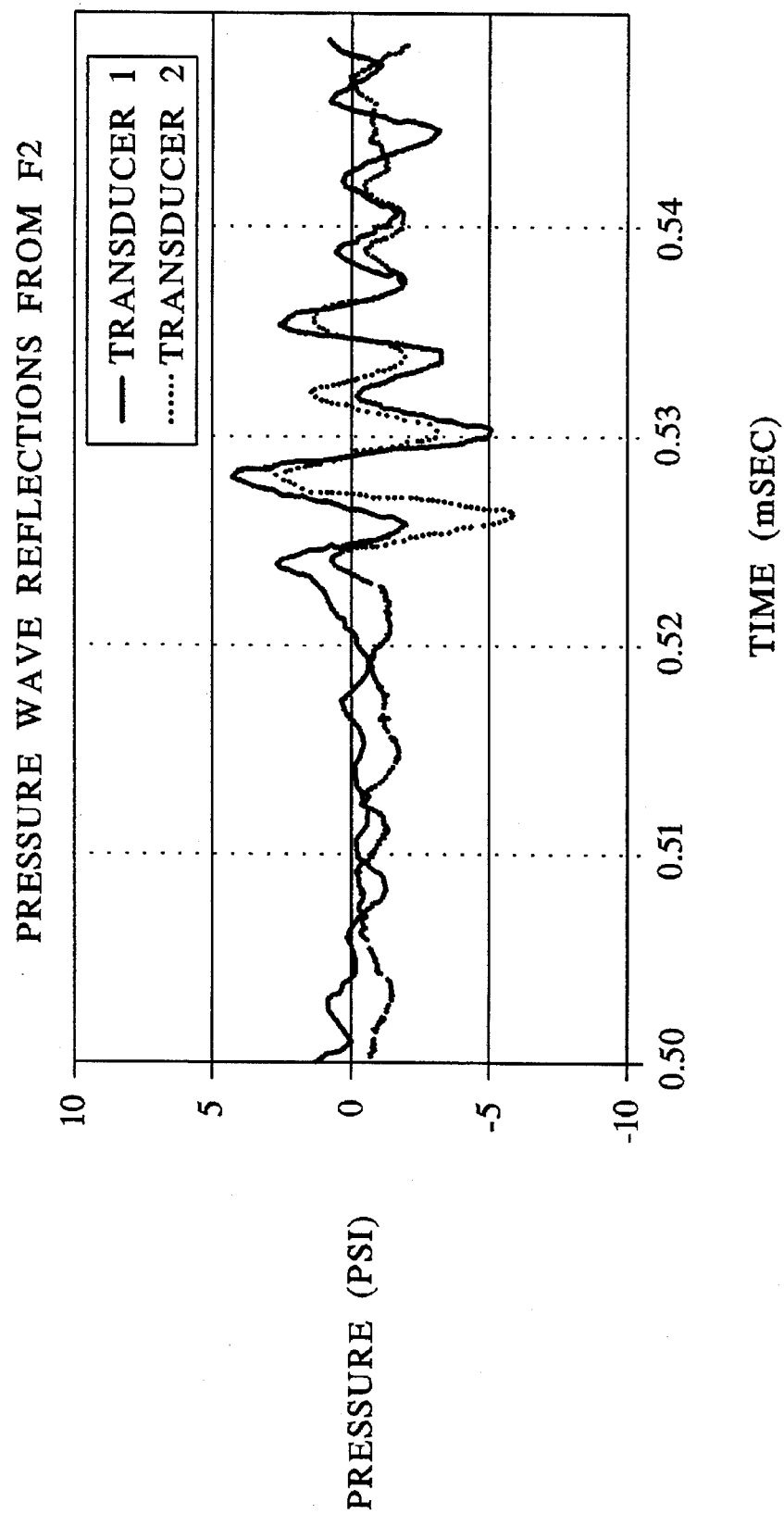
FIG. 3 shows an illustration of pressure wave reflections from a target stone, as detected by two pressure transducers.

FIG. 3 is a graph or typical signals from two pressure transducers, windowed around the arrival time of pressure waves reflected from the target. Each waveform is generated by plotting a number of discrete points, with each point representing a pressure reading taken at some particular time. These data points are plotted sequentially with respect to time from earliest to latest.

As is immediately apparent, the two signals are slightly out of phase (temporally shifted with respect to each other). This slight time shift between the two signals provides information on the difference in distances between the respective transducers and the target, but this information is only accessible if we can measure the time shift with a high degree of accuracy. One method to do so, currently incorporated in this invention in the form of computer software, is as follows:

1) The average pressure of each data set is computed. This value is then subtracted from the pressure value at each data point to remove the DC component of the signal. In doing so, the average value of each data set will be shifted to zero, thereby forcing both data sets to have the same average value.

2) The maximum positive pressure in each data set is determined. The pressure value at every data point is then divided by the maximum positive value for that data set. This operation scales each data set to have a new maximum amplitude of 1.

3) One of the data sets is then shifted in time from its original position by a known amount, and a correlation coefficient calculated to quantitatively determine the agreement between the two data sets, for that time shift. The operation is repeated using a range of time shifts, and a maximum correlation determined. The time shift which maximizes correlation between the two signals corresponds to the difference in signal arrival times at the two transducers, and is the value we wished to measure.

The value of "r" lies between −1 and 1, inclusive, with r=1 indicating complete positive correlation, and r=1 indicating complete negative correlation. A value of r near zero indicates that the two data sets are uncorrelated. In the case of correlating the signals from two pressure sensors, the following technique is adopted. Given two gels of data, each comprised of N discrete data points, we wish to measure how closely the data sets match over their entire lengths. If we were to plot the values of each data point from set one against the values of each data point in set two on a point by point basis, a complete positive correlation would be indicated by a straight line of slope +1. Complete negative correlation would be indicated by a straight line with slope of −1.

For two data sets, $P_1$ and $P_2$, both of length N, it is well known that the correlation coefficient (r), is given by $$r = \frac{\sum_i (P_1 - \overline{P}_1)(P_2 - \overline{P}_2)}{\sqrt{\sum_i (P_1 - \overline{P}_1)^2} \sqrt{\sum_i (P_2 - \overline{P}_2)^2}}, \quad (14)$$

where $\overline{P}_1$ is the mean of the $P_{1i}$'s; $\overline{P}_2$ is the mean of $P_{2i}$'s; and i ranges from 1 to N. NOTE: There are many possible methods for correlating discrete signals. This particular method was chosen for its simplicity, but has yielded good results. Other methods could also be used.

The foregoing description relates to a preferred embodiment of the invention. However, alternative configurations and modifications are possible within the scope of the invention. For example 1, it is further proposed that targets other than concreted stones can be located with this method, provided that the acoustic impedance of the target is substantially different from that of the surrounding media. This method could be employed in locating tumors to be destroyed with ultrasonically induced hyperthermia. For another example, the entire operation of data acquisition and target location could be performed by a custom circuit board or even a custom VLSI (very large scale integration) computer chip. Therefore, the subject matter of the invention is to be limited only by the following claims and their equivalents.

What I claim is:

1. An apparatus for targeting a shock wave in connection with extracorporeal shock wave lithotripsy, comprising in combination:
   a. sensing means for detecting a reflection of the shock wave from a specific target and producing signals corresponding to the reflection at a plurality of predetermined locations wherein the sensing means comprises a plurality of sensors; and
   b. computing means connected to said sensing means for processing said signals so as to identify a three dimensional coordinate location for said target, said computing means comprising correlation means for maximizing a correlation between signals for combinations of the sensors.

2. The apparatus of claim 1 wherein the sensing means comprises a predetermined number of sensors and number of predetermined locations equals the number of sensors.

3. The apparatus of claim 1 wherein the sensing means comprises an array of at least three sensors.

4. The apparatus of claim 1 wherein the sensing means comprise an array of at least four sensors.

5. The apparatus of claim 1 wherein the sensing means comprises piezoelectric elements.

6. The apparatus of claim 1 wherein the sensing means comprises means for converting the signals into a computer readable format and transmitting said signals to said computing means.

7. The apparatus of claim 1 wherein the computing means comprises means for determining the prominent features of the reflection.

8. The apparatus of claim 1 wherein the computing means comprises means for determining the difference in time of the arrival of the reflection at difference sensors.

9. The apparatus of claim 8 wherein the computing means further comprises means for using the time differences to determine the components of a vector extending between the focal point of the shock wave and the target.

10. The apparatus of claim 1 wherein the correlation means further comprises (1) means for determining a prominent feature of the reflection, the prominent feature being defined by the arrival of the reflection of the shock wave at the sensing means from the target;
    (2) means for determining the difference in time of the arrival of the reflection at different sensors; and
    (3) means for using the time differences to determine the components of a vector extending between the focal point of the shock wave and the target.

11. The apparatus of claim 1 further comprising targeting means for adjusting the focal point of the shock wave so as to be coincident with the location of the target.

12. The apparatus of claim 1 further comprising means for adjusting the location of the target so as to be coincident with the location of the focal point of the shock wave.

13. An apparatus for targeting a shock wave in connection with extracorporeal shock wave lithotripsy, comprising in combination:
    a. sensing means for detecting a reflection of a shock wave from a specific target and producing signals corresponding to the reflection at a plurality of predetermined locations wherein the sensing means comprises a plurality of sensors; and
    b. computing means connected to said sensing means for processing said signals so as to identify a three dimensional coordinate location for said target,
       said computing means comprising correlation means for maximizing a correlation between signals for combinations of the senors,
       said computing means further comprising
          means for windowing the signals to obtain windowed signals, each windowed signal comprising a prominent feature of the reflection, and
          means for time-shifting the windowed signals.

14. An improved lithotripter for destroying target stones by extracorporeal shock wave lithotripsy, said lithotripter including a shock wave generator for transmitting one or more shock waves to a predetermined focal point, said improvement comprising in combination:
    a. sensing means for detecting a reflection of the shock wave from a specific target and producing signals corresponding to the reflection at a plurality of predetermined locations wherein the sensing means comprises a plurality of sensors; and
    b. computing means connected to said sensing means for processing said signals so as to identify a three dimensional coordinate location for said target, said computing means comprising correlation means for maximizing a correlation between signals for combinations of the sensors.

15. The apparatus of claim 14 wherein the sensing means comprises a predetermined number of sensors and the number of predetermined locations equals the number of sensors.

16. The apparatus of claim 14 wherein the computing means comprises means for determining the prominent features of the reflection.

17. The apparatus of claim 14 wherein the computing means comprises means for determining the difference in time of the arrival of the reflection at difference sensors.

18. The apparatus of claim 17 wherein the computing means further comprises means for using the time differences to determine the components of a vector extending between the focal point of the shock wave and the target.

19. A method for targeting a shock wave in extracorporeal shock wave lithotripsy, comprising in combination:
    a. generating a first shock wave and detecting a reflection of the first shock wave from a specific target with a plurality of sensors;

b. producing a plurality of signals which correspond to the reflection of the shock wave at a plurality of predetermined locations; and c. processing said signals so as to identify a three dimensional coordinate location for the target, said processing comprising windowing the signal from each sensor to produce a windowed signal, correlating the signals to obtain correlated signals, and time-shifting the correlated signals to maximize a correlation between combinations of the sensors.

* * * * *